United States Patent
Zeng et al.

(10) Patent No.: US 8,430,889 B2
(45) Date of Patent: Apr. 30, 2013

(54) PUNCTURE NEEDLE HOLDER

(75) Inventors: Junhua Zeng, Shenzhen (CN); Zhiwu Chen, Shenzhen (CN); Dahui Zhu, Shenzhen (CN)

(73) Assignee: Shenzhen Mindray Bio-Medical Electronics Co., Ltd, Shenzhen (CN)

( * ) Notice: Subject to any disclaimer, the term of this patent is extended or adjusted under 35 U.S.C. 154(b) by 533 days.

(21) Appl. No.: 12/632,476

(22) Filed: Dec. 7, 2009

(65) Prior Publication Data

US 2010/0168766 A1  Jul. 1, 2010

(30) Foreign Application Priority Data

Dec. 25, 2008 (CN) .......................... 2008 1 0241854

(51) Int. Cl.
*A61B 19/00* (2006.01)
*A61B 17/32* (2006.01)
*A61B 17/34* (2006.01)
*A61B 17/00* (2006.01)

(52) U.S. Cl.
USPC ............... 606/130; 606/167; 606/185; 606/1

(58) Field of Classification Search ........... 606/130, 606/696, 147, 150, 181, 213, 222, 138–139, 606/144–145, 148, 108, 182, 96, 1, 184, 606/44, 122, 123, 177; 600/461, 464, 471, 600/434, 459, 436, 439, 424, 576; 604/116, 604/464, 256, 187, 115, 117–118, 164.01–164.09, 604/178–179, 181, 242–243, 6.05, 170.02; D24/140; 83/94; 112/80.4

See application file for complete search history.

(56) References Cited

U.S. PATENT DOCUMENTS

| | | | | |
|---|---|---|---|---|
| 2,402,306 A | * | 6/1946 | Turkel | 604/174 |
| 2,525,398 A | * | 10/1950 | Collins | 604/179 |
| 3,538,915 A | * | 11/1970 | Frampton et al. | 604/272 |
| 4,058,114 A | * | 11/1977 | Soldner | 600/461 |
| 4,346,717 A | * | 8/1982 | Haerten | 600/461 |
| 4,378,813 A | * | 4/1983 | Lovelace et al. | 600/587 |
| 4,402,324 A | * | 9/1983 | Lindgren et al. | 600/461 |
| 4,469,106 A | * | 9/1984 | Harui | 600/461 |
| 4,635,644 A | * | 1/1987 | Yagata | 600/464 |
| 4,638,799 A | * | 1/1987 | Moore | 606/1 |
| 4,706,665 A | * | 11/1987 | Gouda | 606/130 |
| 4,733,661 A | * | 3/1988 | Palestrant | 606/108 |
| 4,841,967 A | * | 6/1989 | Chang et al. | 606/130 |
| 4,883,053 A | * | 11/1989 | Simon | 606/130 |
| 4,899,756 A | * | 2/1990 | Sonek | 600/461 |
| 4,911,173 A | * | 3/1990 | Terwilliger | 600/464 |
| 5,024,665 A | * | 6/1991 | Kaufman | 604/179 |
| 5,076,279 A | * | 12/1991 | Arenson et al. | 600/461 |
| 5,196,019 A | * | 3/1993 | Davis et al. | 606/130 |
| 5,221,264 A | * | 6/1993 | Wilk et al. | 604/167.01 |

(Continued)

FOREIGN PATENT DOCUMENTS

| | | |
|---|---|---|
| CN | 2040769 U | 7/1989 |
| CN | 2103320 U | 5/1992 |
| CN | 1575776 A | 2/2005 |

*Primary Examiner* — Gary Jackson
*Assistant Examiner* — Richard Louis
(74) *Attorney, Agent, or Firm* — Kory D. Christensen; Stoel Rives LLP

(57) ABSTRACT

A puncture needle holder comprising a base frame, a link bar, a first seat part, a second seat part, and a positioning mechanism is disclosed.

10 Claims, 6 Drawing Sheets

U.S. PATENT DOCUMENTS

| | | | |
|---|---|---|---|
| 5,235,987 A * | 8/1993 | Wolfe | 600/461 |
| 5,623,931 A * | 4/1997 | Wung et al. | 600/461 |
| 5,758,650 A * | 6/1998 | Miller et al. | 600/461 |
| 5,941,889 A * | 8/1999 | Cermak | 606/130 |
| 6,203,499 B1 * | 3/2001 | Imling et al. | 600/461 |
| 6,228,064 B1 * | 5/2001 | Abita et al. | 604/179 |
| 6,283,942 B1 * | 9/2001 | Staehlin et al. | 604/116 |
| 6,296,614 B1 * | 10/2001 | Pruter | 600/461 |
| 6,361,499 B1 * | 3/2002 | Bates et al. | 600/461 |
| 6,379,307 B1 * | 4/2002 | Filly et al. | 600/461 |
| 6,485,426 B2 * | 11/2002 | Sandhu | 600/461 |
| 7,022,082 B2 * | 4/2006 | Sonek | 600/461 |
| 7,588,541 B2 * | 9/2009 | Floyd et al. | 600/461 |
| 7,727,192 B2 * | 6/2010 | Tokumoto et al. | 604/116 |
| 7,832,346 B2 * | 11/2010 | Hattori | 112/78 |
| 8,073,529 B2 * | 12/2011 | Cermak et al. | 600/424 |
| 8,137,281 B2 * | 3/2012 | Huang et al. | 600/461 |
| 8,147,408 B2 * | 4/2012 | Bunce et al. | 600/437 |
| 8,241,301 B2 * | 8/2012 | Zhang et al. | 606/130 |
| 2002/0038117 A1 * | 3/2002 | Tokita et al. | 606/1 |
| 2003/0212414 A1 * | 11/2003 | Sonek | 606/130 |
| 2004/0092821 A1 * | 5/2004 | Hering et al. | 600/459 |
| 2005/0059891 A1 * | 3/2005 | Kosaku | 600/439 |
| 2005/0131291 A1 * | 6/2005 | Floyd et al. | 600/424 |
| 2005/0143753 A1 * | 6/2005 | Whitmore et al. | 606/130 |
| 2005/0267373 A1 * | 12/2005 | Lee | 600/471 |
| 2006/0020211 A1 * | 1/2006 | Tokumoto et al. | 600/464 |
| 2006/0129046 A1 * | 6/2006 | Stevens et al. | 600/464 |
| 2006/0229641 A1 | 10/2006 | Gupta et al. | |
| 2006/0241477 A1 * | 10/2006 | Sasady et al. | 600/464 |
| 2007/0038113 A1 * | 2/2007 | Oonuki et al. | 600/464 |
| 2007/0049822 A1 * | 3/2007 | Bunce et al. | 600/437 |
| 2008/0015624 A1 * | 1/2008 | Sonoda et al. | 606/185 |
| 2008/0183191 A1 * | 7/2008 | Schoepp | 606/130 |
| 2009/0171219 A1 * | 7/2009 | Uchibori | 600/461 |
| 2009/0192469 A1 * | 7/2009 | Bognar | 604/177 |
| 2010/0041990 A1 * | 2/2010 | Schlitt et al. | 600/439 |
| 2010/0125283 A1 * | 5/2010 | Butcher et al. | 606/130 |
| 2010/0228131 A1 * | 9/2010 | Oonuki et al. | 600/461 |
| 2010/0278785 A1 * | 11/2010 | Schwaiger et al. | 424/93.7 |
| 2010/0280354 A1 * | 11/2010 | Zhang et al. | 600/411 |

* cited by examiner

PUNCTURE NEEDLE HOLDER

CROSS-REFERENCE TO RELATED APPLICATIONS

This application claims priority to Chinese Patent Application No. 200810241854.3, filed on Dec. 25, 2008, which is hereby incorporated by reference in its entirety.

TECHNICAL FIELD

The present disclosure relates to a puncture needle holder.

BRIEF SUMMARY

A puncture needle holder according to one embodiment includes a base frame, a link bar, a first seat part, a second seat part, and a positioning mechanism. Additional aspects will be apparent from the following detailed description, which proceeds with reference to the accompanying drawings.

DETAILED DESCRIPTION

Figure 1:
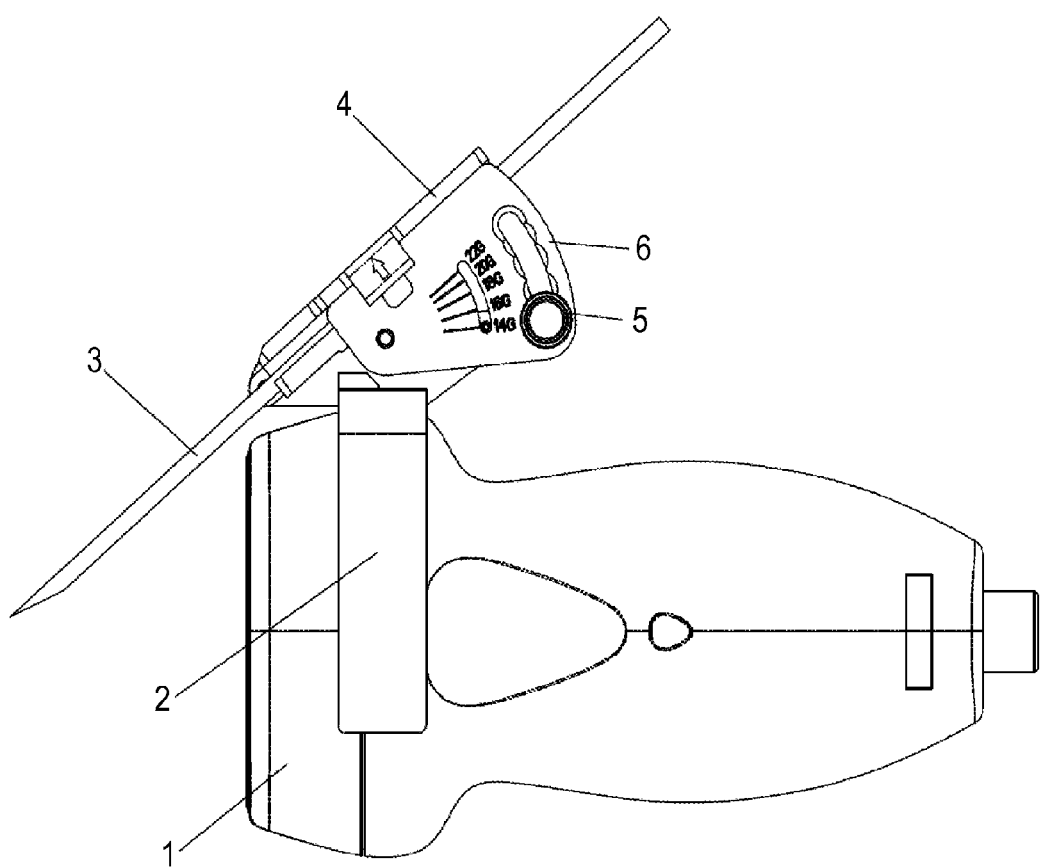
FIG. 1 is a schematic structural view illustrating a connection between a puncture needle holder and an ultrasonic probe.

When a medical practitioner extract cells or organ tissue samples from a patient or inject medication into the patient, a puncture needle of certain size should be mounted to a puncture needle holder, and the puncturing (piercing) operation is conducted at a preset angle. A conventional type of needle holder generally comprises a needle seat with an aperture. Needle seats of different sizes are required when needles of different sizes are needed in a puncturing operation. Another type of needle holder is provided with a catheter in a hole of a needle seat. Needles of different sizes are fitted in catheters of different diameters. For the above-mentioned two types of holders, different holders or catheters must be replaced to match needles of different sizes. Furthermore, holders often include many accessories, which increase management complexity, as well as the risk of loss of the accessories, and make operation inconvenient.

The puncture needle holder of the present disclosure is provided with fewer accessories, is easy to operate, and is applicable to needles of different sizes. To this end, one embodiment of a puncture needle holder comprises a base frame, a link bar, a first seat part, a second seat part, and a positioning mechanism. The link bar may be pivotably connected to the base frame and may have a pivot axis. The link bar may have a support portion and a control portion. A guiding space for guiding the puncturing of the puncture needle may be formed between the first seat part and the second seat part. The first seat part may be movably supported by the support portion and the second seat part may be located on the base frame. The base frame may have a guiding body for constraining the first seat part and causing the first seat part to generate a displacement component in a direction perpendicular to the puncturing direction when the first seat part is moved.

The guiding body may cooperate with the first seat part, and the positioning mechanism may be connected with the link bar and the base frame and locks the link bar relative to the base frame after the link bar moves into place. The link bar may be able to be pivoted by manipulating the control portion, so that the link bar moves together with the first seat part to adjust the size of the guiding space. By operating the link bar, the movement of the first seat part is controlled to adjust the distance between the first and second seat parts, so that guiding spaces of different sizes may be provided for use with puncture needles of different sizes. As a result, there can be fewer accessories, the cost is lowered, and ease of operation is increased.

The embodiments of the disclosure will be best understood by reference to the drawings, wherein like elements are designated by like numerals throughout. In the following description, numerous specific details are provided for a thorough understanding of the embodiments described herein. However, those of skill in the art will recognize that one or more of the specific details may be omitted, or other methods, components, or materials may be used. In some cases, operations are not shown or described in detail in order to avoid obscuring more important aspects of the disclosure.

Furthermore, the described features, operations, or characteristics may be combined in any suitable manner in one or more embodiments. It will also be readily understood that the order of the steps or actions of the methods described in connection with the embodiments disclosed may be changed as would be apparent to those skilled in the art. Thus, any order in the drawings or detailed description is for illustrative purposes only and is not meant to imply a required order, unless specified to require an order.

Figure 2:
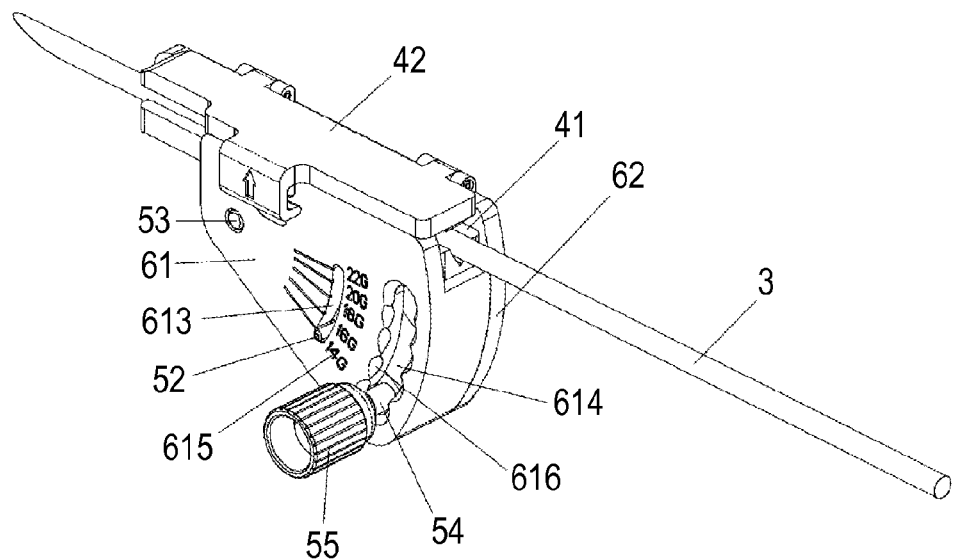
FIG. 2 is a schematic structural view of the puncture needle holder with a closed needle seat.
Figure 3:
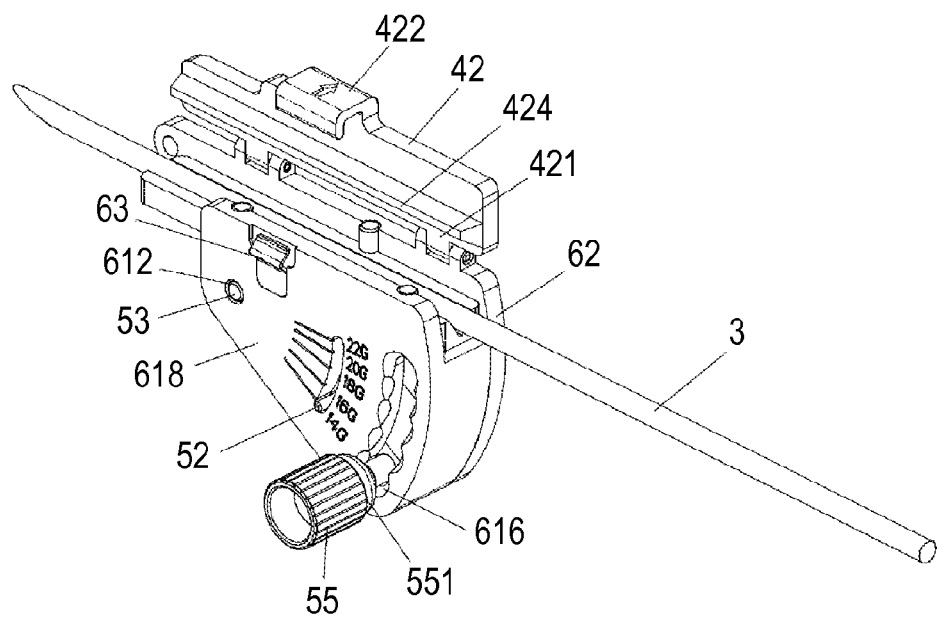
FIG. 3 is a schematic structural view of the puncture needle holder with an open needle seat.
Figure 4:
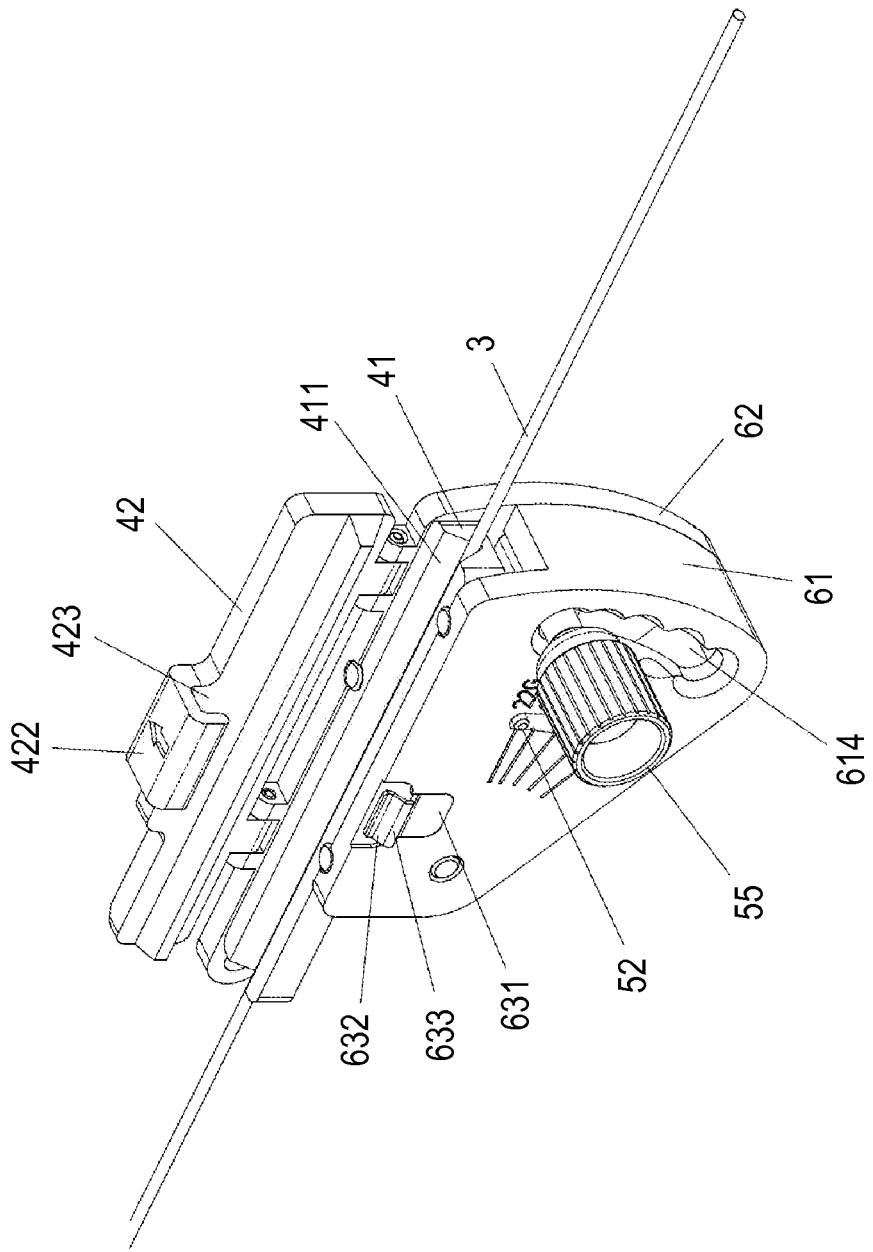
FIG. 4 is a schematic structural view of the puncture needle holder after an operating position is adjusted.
Figure 5:
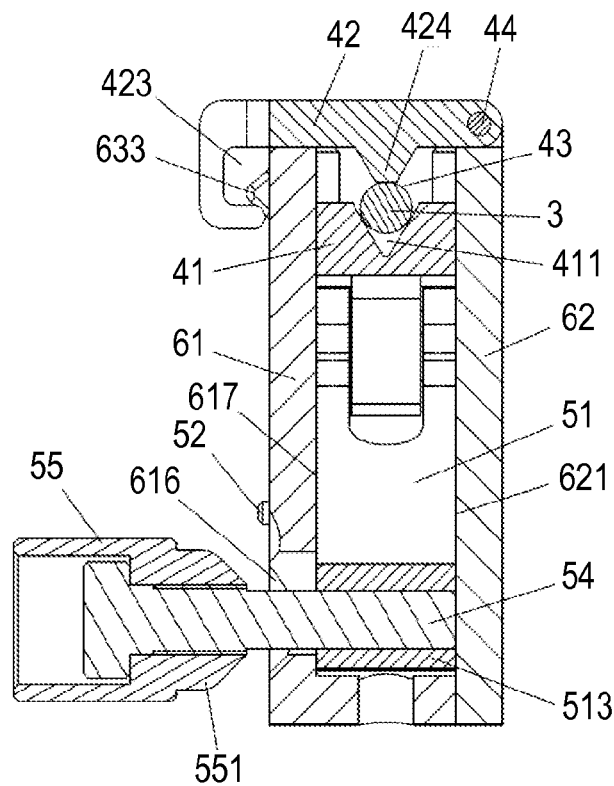
FIG. 5 is a transverse sectional view of the puncture needle holder.
Figure 6:
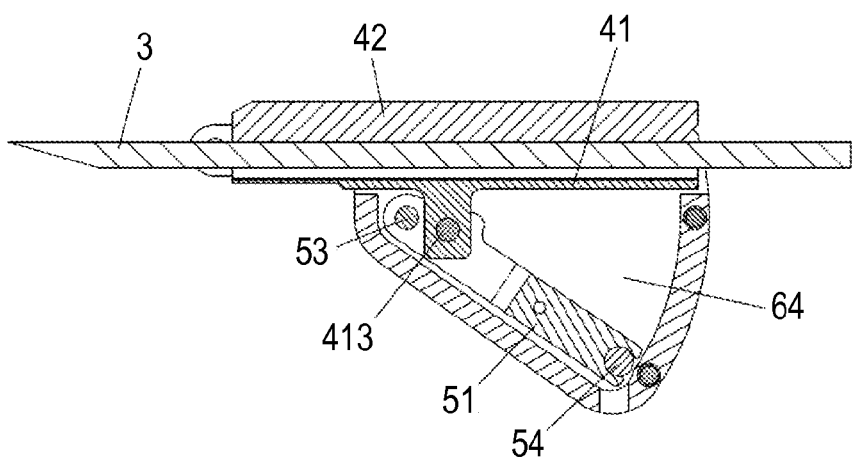
FIG. 6 is a longitudinal sectional view of the puncture needle holder.
Figure 7:
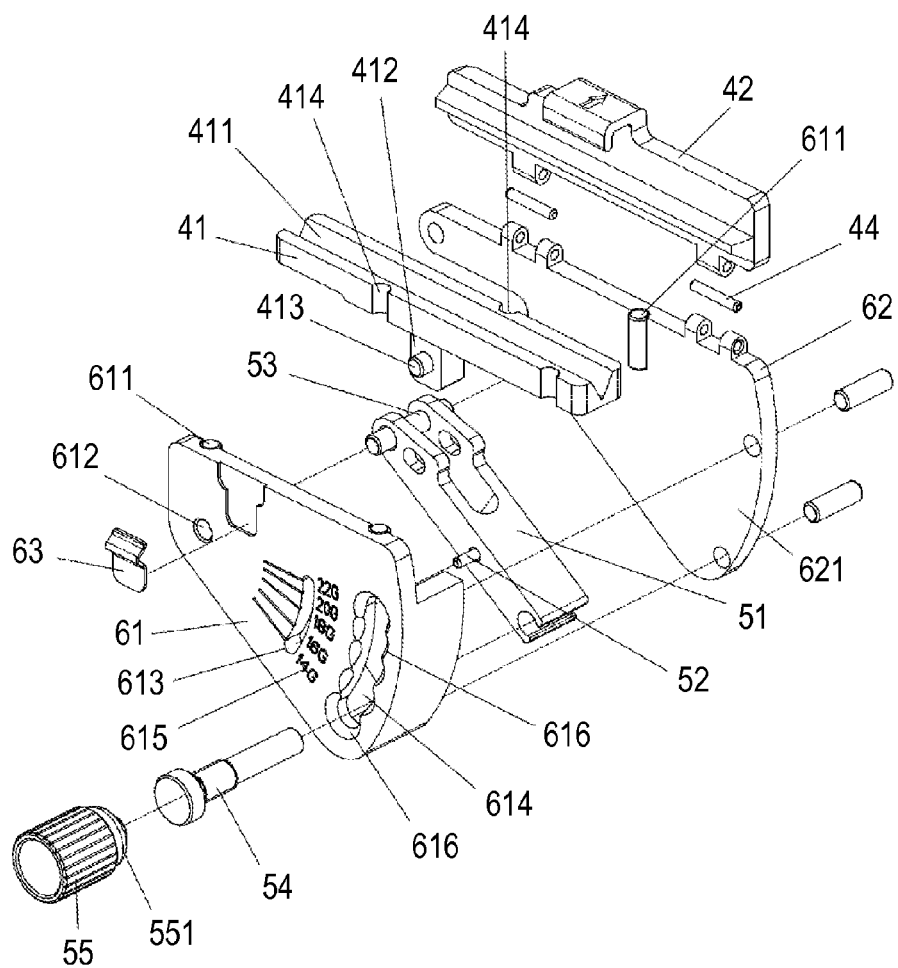
FIG. 7 is a perspective exploded view of the puncture needle holder.
Figure 8:
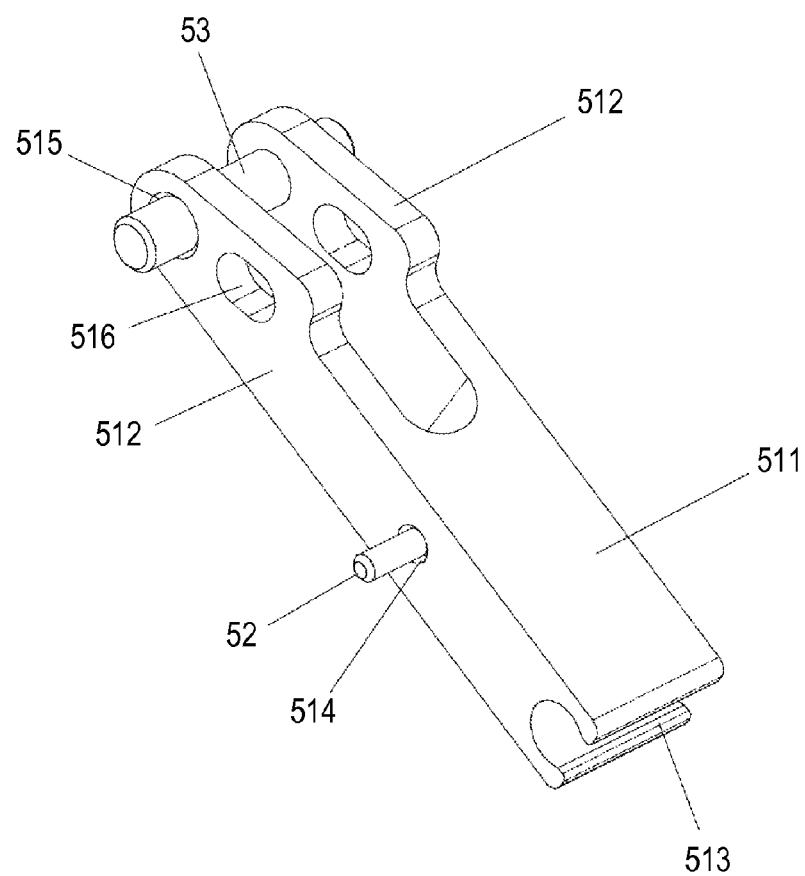
FIG. 8 is a perspective view of a connecting bar of the puncture needle holder.

Referring to FIGS. 1 through 8, one embodiment of puncture needle holder comprises a base frame 6, an adjusting mechanism 5, and a needle seat 4. The needle seat 4 has a guiding space 43 for guiding the puncturing of the needle 3. The holder is generally connected with an ultrasonic probe 1 by a clamping mechanism 2. The needle 3 is engaged in the needle seat 4, which is mounted on the base frame 6, and the size of guiding space 43 is adjustable by an adjusting mechanism 5.

The base frame 6 comprises a first frame part 61 and a second frame part 62, which are fixedly connected together. The first frame part 61 has an internal surface 617 facing toward the second frame part 62, and an external surface 618 facing away from the second frame part 62. The internal surface 617 is provided with a guiding portion such as protruded guiding block 611. A mounting hole 612, an arc-shaped indication slot 613, and an arc-shaped adjustment slot 614 are formed through the internal and external surface 617 and 618.

The indication slot 613 and the adjustment slot 614 are located, in one embodiment, at the same side of the first frame part with the mounting hole 612. The center of the mounting hole 612 is coincident to the center of the arcs of the indication slot and the adjustment slot. The indication slot 613 is located between the mounting hole 612 and the adjustment slot 614.

A plurality of circumferentially arranged operating position markers 615 are formed close to the indication slot 613 on the external surface 618 of the first frame part, and the positions of operating position markers 615 can be clearly identified by the help of the indication slot 613. A plurality of circumferentially arranged locking recesses 616 are formed along an edge of the adjustment slot 614 in circumferential positions corresponding to the operating position markers 615.

A leaf spring 63 that is resiliently deformable is fixed to the external surface 618 of the first frame part 61. The leaf spring 63 has a fixed segment 631 and a free segment 632, which are integrally formed by bending. The fixed segment 631 is fixed to the external surface 618. The free segment 632 extends like a cantilever and has an arc-shaped out-bending part 633. An internal surface 621 of the second frame part 62 that faces toward the first frame part 61 is also provided with a guiding body, protruded guiding block 611. The second frame part 62 is also provided with a mounting hole that is corresponding to the mounting hole 612 of the first frame part 61.

In one embodiment, the needle seat 4 comprises a first seat part 41 and a second seat part 42, which are individually provided and between which a guiding space 43 for guiding the puncturing of the puncture needle 3 is formed. The upper surface of the first seat part 41 is formed with a recessed V-shaped engaging slot 411. The lower surface of the first seat part 41 is formed with a protruded slider 412 that is integrally provided with a connecting stud 413. The left and right sides of the first seat part 41 are each provided with a guiding slot 414, which is engagable by the guiding body, guiding block 611, of the first or second frame part. The second seat part 42 has a mounting end 421 which is pivotably attached to the second frame part 62 via a pivot pin 44 and a snap end 422, which is formed with a snap slot 423 that is engagable by the out-bending part 633 of the leaf spring 63. A lower surface of the second seat part 42 that faces toward the first seat part 41 is provided with a protruded V-shaped engaging block 424. The guiding space 43 is formed between the engaging block 424 and the engaging slot 411 of the first seat part 41. Since the second seat part 42 is pivotably attached to the second frame part 62, the second seat part 42 can be pivoted within a certain angle range with respect to the second frame part 62.

In the depicted embodiment, the adjusting mechanism 5 comprises a link bar 51, an indicator rod 52, and a pivoting pin 53. The link bar 51 comprises a base section 511 having a control portion 513 at an end and two extension sections 512 extending integrally and parallel with each other from the other end of the base section 511. An indicator hole 514 is provided on the base section 511 at a position that corresponds to the indication slot 613 of the first frame part, with the indicator rod 52 fixedly inserted into the indicator hole. Each of the extension sections 512 is formed with a pin hole 515 and a support portion, such as sliding slot 516 therethrough. The pin hole 515 and the support portion, sliding slot 516, are spaced apart with a certain distance. The distance between the pin hole 515 and the support portion, sliding slot 516, may be much smaller than the distance between the pin hole 515 and the control portion 513.

With the pin hole 515 as the center of pivoting and with the same angle of pivoting, a small movement of the support portion, sliding slot 516, corresponds to a large movement of the control portion 513, hence increasing the control precision. The support portion, sliding slot 516, is engaged by the connecting stud 413 of the first seat part 41. The connecting stud 413 inserts into the support portion, sliding slot 516, to form a sliding pair with the latter. The length of the support portion, sliding slot 516, is larger than the diameter of the connecting stud 413. Given that the connecting stud 413 can smoothly slide in the support portion, sliding slot 516, the width of the support portion, sliding slot 516, should be close to the diameter of the connecting stud 413 as much as possible, so that, when the link bar 51 is pivoted, the first seat part 41 can move linearly and as smoothly as possible, and vertical back lash can be reduced.

The adjusting mechanism further comprises a positioning mechanism for realizing relative positioning between the link bar 51 and the base frame 6 when the link bar 51 is pivoted into place. In one embodiment, the positioning mechanism comprises a connecting screw 54 and a locking nut 55 having a locking protrusion 551. However, an artisan will recognize that other types of positioning mechanisms may be used.

In the depicted embodiment, the first frame part 61 is fixedly attached to the second frame part 62. A cavity 64 is formed between the internal surface 617 of the first frame part 61 and the internal surface 621 of the second frame part 62. The link bar 51 is placed inside the cavity 64. The middle section of the pivoting pin 53 passes through the pin holes 515 of the extension sections 512 of the link bar. The opposite ends of the pivoting pin 53 are inserted into the mounting holes 612 of the first and second frame part 61, 62, respectively, to form rotating pairs therewith, so that the link bar 51 is pivotable around the pivoting pin 53.

The first seat part 41 is parallel to the second seat part 42. The snap slot 423 of the second seat part 42 is engaged by the out-bending part 633 of the leaf spring 63 so as to attach the second seat part 42 to the first and second frame part 61, 62. The guiding bodies, guiding blocks 611, of the first and second frame parts are inserted into the guiding slots 414 of the first seat part 41 to form guided moving pairs therewith. The slider 412 of the first seat part 41 is located between the two extension sections 512 of the link bar 51. The connecting stud 413 of the first seat part 41 passes into the support portions, sliding slots 516, of the two extension sections 512 respectively.

When the link bar 51 is pivoted around the pivoting pin 53, the connecting stud 413 slides in the support portion, sliding slot 516, and causes the first seat part 41 to move linearly along the guiding body, guiding block 611. The first seat part 41 is movably supported in the support portion, sliding slot 516, as a support and moves linearly in a direction perpendicular to the puncturing direction under the constraint of the guiding body, guiding block 611, so that during movement, the first seat part 41 and the second seat part 42 keep parallel with each other and will not be misaligned.

In one embodiment, the indicator rod 52 is inserted through the indication slot 613 of the first frame part 61 and into the indicator hole 514 of the base section of the link bar. The indicator rod 52 slides in the indication slot 613 as the link bar 51 is pivoted and is aligned to one of the operating position markers 615 on the first frame part 61. The connecting screw 54 is transversely inserted through the adjustment slot 614 of the first frame part 61. One end of the connecting screw 54 is fixed, e.g., adhered or welded, to the link bar control portion 513. The other end of the connecting screw 54 is connected with the locking nut 55 by screwing. The locking protrusion 551 of the locking nut 55 engages with the locking recess 616 of the first frame part 61.

Each operating position marker 615 corresponds to an operating position, which, in turn, corresponds to one of the various pivoting angles of the link bar 51, i.e. one of the various distances of the first and second seat part 41, 42, as well as one of the various sizes of the guiding space 43. Various guiding spaces 43 correspond to puncture needles 3 of various respective sizes. At each of the operating positions, the indicator rod 52 corresponds to one of the operating position markers 615.

The locking protrusion 551 of the locking nut 55 is engaged in the locking recess 616 corresponding to this operating position to realize relative positioning between the link bar 51 and the base frame 6. When a puncture needle is to be replaced by a needle of a different size, the locking nut 55 on the connecting screw 54 will be moved from one of the locking recesses to another for switching the operating positions.

A process according to one embodiment is as follows. First, with the second seat part 42 in an open state and the original needle removed, the locking nut 55 is screwed out to cause the locking protrusion 551 thereof leaving the locking recess 616. The locking nut 55 is caused to move so that the locking nut 55 and the connecting screw 54 slide in the adjustment slot 614. With the indication of the operating position markers 615, when desired operating position is reached, the locking nut 55 is screwed in again to cause the locking protrusion 551 of the locking nut 55 and the locking recess 616 in this operating position to abut against each other closely. Thus, it is able to fix the link bar 51 and the first seat part 41 at a specified operating position and to mount a new puncture needle 3 of a corresponding size between the first seat part 41 and the second seat part 42.

After mounting the newly replaced needle 3 into the engaging slot 411 of the first seat part 41, the second seat part 42 is pivoted to cause the out-bending part 633 of the leaf spring 63 to snap into the snap slot 423 of the second seat part 42, and thus the second seat part 42 is fixed to the base frame 6 with the engaging block 424 of the second seat part 42 pressed onto the puncture needle 3. Alternatively, when switching the operating positions, the second seat part 42 may not be opened, and a puncture needle 3 of a corresponding size is directly placed in after the operating position has been adjusted.

In addition, after a medical person or an operator finishes the puncturing operation to the body of the patient, he or she may simply push the snap end 422 of the second seat part 42 slightly to disconnect the snap slot 423 from the leaf spring 63 quickly, allowing the needle 3 to be released in a convenient and labor-saving manner. After taking away the probe and the holder, the needle is left attached to the body of the patient for a medical procedure.

The puncture needle holder comprises a base frame, a link bar, a first seat part, a second seat part, and a positioning mechanism. The link bar is pivotably connected to the base frame and has a pivot axis. The link bar has a support portion and a control portion. A guiding space for guiding the puncturing of the puncture needle is formed between the first seat part and the second seat part. The first seat part is movably supported by the support portion, and the second seat part is located on the base frame.

The base frame has a guiding body for constraining the first seat part and causing the first seat part, when moved, to create a displacement in a direction perpendicular to the puncturing direction. The guiding body cooperates with the first seat part. The positioning mechanism connects the link bar and the base frame and locates the link bar relative to the base frame after the link bar moves into place. When operating at the control portion, the link bar is pivoted and drives the first seat part to move, to adjust the size of the guiding space for use with puncture needles of different sizes, hence reducing accessories, lowering costs, and facilitating ease of operation.

Between the first seat part and the second seat part, there may be a recessed V-shaped structure and a protruded V-shaped structure, respectively, for forming the guiding space of needle. Alternatively, there may be U-shaped structures or structures of other shapes that may form the guiding space. The base frame may comprise a first frame part and a second frame part that are permanently attached to each other, or there may be an integrated base frame, or the base frame may be comprised of more than two parts.

The support portion supports the first seat part, such that the support portion can drive the first seat part to move linearly along the guiding body of the base frame when the link bar is pivoted. The control portion receives an external action force such that the link bar may be driven to pivot about the pivot axis by operating the control portion. The support portion and the control portion may locate at the same side of the pivot axis, or may locate on opposite sides of the pivot axis respectively. When the support portion and the control portion are at the same side of the pivot axis and the distance between the support portion and the pivot axis is smaller than that between the control portion and the pivot axis, the entire link bar is more compact and it is possible to reflect the small movement of the first seat part by the large movement of the control portion, which enables the control portion to move for a larger distance and realizes operating position control.

The connecting structure between the link bar and the first seat part may be formed by two extension sections of the link bar with and one slider of the first seat part. Alternatively, the link bar may have one extension section and the first seat part have two sliders. In both ways, the supported area of the first seat part will be subjected to uniform forces and move smoothly. Alternatively, it is also possible that the link bar has only one extension section, and the first seat part has only one slider. In still other embodiments, the link bar and the first seat part may have a plurality of extension sections and sliders for connection.

The positioning mechanism realizes relative positioning of the link bar and the base frame after the link bar is pivoted into place. The positioning mechanism may comprise a friction positioning mechanism formed between the link bar and the base frame, such as a damping shaft or any other structure that enables the link bar to stop at an arbitrary position within its pivoting angle range. The positioning mechanism may comprise a connecting screw and a locking nut connected with the connecting screw by screwing. The locking nut has a locking protrusion, and the base frame has a locking recess. Relative positioning is realized by the engagement between the locking protrusion and the locking recess. Alternatively, the positioning mechanism may be configured to lock the link bar by a threaded fastener after the link bar is pivoted into place. A positioning structure comprising an out-bending part of a leaf spring and a groove, or any other devices for achieving the same function, may also be used.

The guiding body of the base frame may comprise a protruded guiding block or a recessed guiding slot. The first seat part has thereon a guiding slot or guiding block matching with the guiding body of the base frame. The guiding block may be circular, elliptical, square shaped, or polygonal. The guiding body may also comprise other structures that can make the first seat part move linearly in a predetermined direction. Under the constraint of the guiding body of the base frame, the first seat part may only move linearly in a direction perpendicular to the puncturing direction, that is, only generate a displacement component perpendicular to the puncturing direction (in this condition the displacement component along the puncturing direction is zero). Alternatively, the first seat part may move in an oblique direction along the guiding body, that is, generate displacement components in both the puncturing direction and the direction perpendicular to the puncturing direction.

The link bar is pivoted around the pivot axis. This may be achieved by a shaft-hole fitting structure. For example, the link bar is provided with a shaft and the base frame is provided with a hole, or vice versa. When the link bar is pivoted, the link bar and the shaft may rotate together, or the link bar may itself rotate around the shaft. The link bar may also be pivoted relative to the base frame via a hinge. Alternatively, the link bar may be frictionally fit with the base frame, such that the link bar is pivoted against a friction surface which constrains the link bar. Alternatively, the link bar is pivoted by means of other structures.

The second seat part may have a mounting end and a snap end. The mounting end is pivotably attached to the base frame. The base frame has a snapping part which engages with the snap end to enable the second seat part to pivot with respect to the base frame. When pivoting, it is possible to pivot the second seat part directly with respect to the base frame, or pivot the base frame with respect to the second seat part. The snap end may be arranged on the second seat part while the snapping part is arranged on the base frame. It is also possible that the snap end is arranged on the base frame and the snapping part on the second seat part. The snapping part may be a resilient leaf spring, which not only simplifies the structure of the snapping part but also realizes convenient, fast, and labor-saving operations. In addition, the second seat part may be also engaged to the base frame directly, or be fastened on the base frame via a fastener, or engaged with the base frame via frictional fitting or other mounting structures.

In order to adjust operating positions in a clear and visualized manner, an indication slot is provided on the base frame and an indicator rod is provided on the link bar. The indicator rod is inserted through the indication slot and is movable along the indication slot. The base frame is also provided with at least two operating position markers, each of which corresponds to an operating position. At each of the operating positions, the indicator rod is aligned to the operating position marker of this operating position. Alternatively, it is also possible not to provide operating position markers. In this case, it may adjust the position of the first seat part after placing the puncture needle into the first seat part and the second seat part, to clamp the puncture needle by the first seat part and the second seat part.

It will be understood by those having skill in the art that many changes may be made to the details of the above-described embodiments without departing from the underlying principles of the invention. The scope of the present invention should, therefore, be determined only by the following claims.

The invention claimed is:

1. A puncture needle holder comprising a base frame, a link bar, a first seat part, a second seat part, and a positioning mechanism, wherein the link bar is pivotably connected to the base frame and has a pivot axis, the link bar has a support portion and a control portion, a guiding space for guiding the puncturing of a puncture needle is formed between the first seat part and the second seat part, the first seat part is slidably supported by the support portion and the second seat part includes a mounting end attached to the base frame, the base frame has a guiding body for constraining the first seat part and causing the first seat part to generate displacement in a direction perpendicular to the puncturing direction when the first seat part is moved, the guiding body cooperates with the first seat part, the positioning means is connected with the link bar and the base frame and locks the link bar relative to the base frame after the link bar moves into place, the link bar is able to be pivoted by manipulating the control portion, so that the link bar moves together with the first seat part to adjust the size of the guiding space, and the first seat part and the second seat part are able to keep parallel with each other during adjustment of the size of the guiding space.

2. The puncture needle holder according to claim 1, wherein the support portion and the control portion are arranged at the same side of the pivot axis, and the distance between the support portion and the pivot axis is smaller than the distance between the control portion and the pivot axis.

3. The puncture needle holder according to claim 1, wherein the positioning mechanism comprises a connecting screw and a locking nut, the base frame is provided with an adjustment slot through which the connecting screw extends, one end of the connecting screw is fixed to the control portion, the other end of the connecting screw is connected with the locking nut by screwing, the base frame has at least two locking recesses along an edge of the adjustment slot, and the locking nut has a locking protrusion is configured to engage with one of the locking recesses.

4. The puncture needle holder according to claim 3, wherein the link bar is provided with an indicator rod, the base frame is provided with an indication slot, the indicator rod is inserted through the indication slot and is movable along the indication slot, the base frame is provided with at least two operating position markers corresponding to the locking recesses respectively, and at each operating position, the indicator rod is aligned to one of the operating position markers corresponding to this operating position.

5. The puncture needle holder according to claim 1, wherein the support portion comprises one of a sliding slot and a connecting stud, the first seat part is correspondingly provided with the other of the sliding slot and the connecting stud, and the connecting stud is inserted into the sliding slot and is slidable in the sliding slot.

6. The puncture needle holder according to claim 5, wherein the link bar comprises a base section and an extension section integrally extending from the base section, the control portion is formed in the base section, the sliding slot is formed in the extension section, and the first seat part is provided with a slider on which the connecting stud is provided.

7. The puncture needle holder according to claim 1, wherein a surface of the first seat part that faces toward the second seat part is provided with one of a recessed engaging slot and a protruded engaging block, a surface of the second seat part that faces toward the first seat part is correspondingly provided with the other of the recessed engaging slot and the protruded engaging block, and the guiding space is formed between the engaging slot and the engaging block.

8. The puncture needle holder according to claim 7, wherein the second seat part has a mounting end and a snap end, the mounting end is pivotably attached to the base frame, and the base frame is provided with a snapping part which is engageable by the snap end.

9. The puncture needle holder according to claim 8, wherein the snapping part is a resilient deformable leaf spring having a fixed segment fixed to the base frame and a free segment extending like a cantilever, the free segment being engageable by the snap end.

10. The puncture needle holder according to claim 1, wherein the guiding body is one of a guiding block and a guiding slot, the first seat part is correspondingly provided with the other of the guiding slot and the guiding block, and the guiding block is engagable into the guiding slot.

* * * * *